(12) United States Patent
Okubo et al.

(10) Patent No.: US 11,453,931 B2
(45) Date of Patent: Sep. 27, 2022

(54) MEDICAL AU-PT-PD ALLOY

(71) Applicants: TANAKA KIKINZOKU KOGYO K.K., Tokyo (JP); TOKUSHIMA UNIVERSITY, Tokushima (JP)

(72) Inventors: Michimasa Okubo, Isehara (JP); Kenji Goto, Isehara (JP); Kunihiro Tanaka, Isehara (JP); Kojiro Shiraishi, Isehara (JP); Kunihiro Shima, Isehara (JP); Yuya Kato, Isehara (JP); Kenichi Hamada, Tokushima (JP); Eiichi Honda, Tokushima (JP); Emi Takegawa, Tokushima (JP)

(73) Assignees: TANAKA KIKINZOKU KOGYO K.K., Tokyo (JP); TOKUSHIMA UNIVERSITY, Tokushima (JP)

( * ) Notice: Subject to any disclaimer, the term of this patent is extended or adjusted under 35 U.S.C. 154(b) by 0 days.

(21) Appl. No.: 17/607,397

(22) PCT Filed: Sep. 24, 2020

(86) PCT No.: PCT/JP2020/035903
§ 371 (c)(1),
(2) Date: Oct. 29, 2021

(87) PCT Pub. No.: WO2021/060314
PCT Pub. Date: Apr. 1, 2021

(65) Prior Publication Data
US 2022/0213576 A1 Jul. 7, 2022

(30) Foreign Application Priority Data
Sep. 26, 2019 (JP) .............................. JP2019-175208

(51) Int. Cl.
*C22C 5/02* (2006.01)
*C22C 1/02* (2006.01)

(52) U.S. Cl.
CPC . *C22C 5/02* (2013.01); *C22C 1/02* (2013.01)

(58) Field of Classification Search
CPC ....................................................... C22C 5/02
See application file for complete search history.

(56) References Cited

U.S. PATENT DOCUMENTS

| 2,071,216 | A | | 2/1937 | Powell et al. |
| 4,062,676 | A | * | 12/1977 | Knosp .................... A61K 6/844 |
| | | | | 420/509 |

(Continued)

FOREIGN PATENT DOCUMENTS

| EP | 3 015 559 A1 | 5/2016 |
| JP | H09-125223 A | 5/1997 |

(Continued)

OTHER PUBLICATIONS

Mireille Harmelin, Volodymyr Ivanchenko (2006), Au-Pd-Pt (Gold—Palladium—Platinum); Landolt-Bbrnstein—Group IV Physical Chemistry 11B (Noble Metal Systems. Selected Systems from Ag-Al-Zn to Rh-Ru-Sc) G. Effenberg, S. Ilyenko (ed.), (Year: 2006).*

(Continued)

*Primary Examiner* — Christopher S Kessler
(74) *Attorney, Agent, or Firm* — Foley & Lardner LLP (57) ABSTRACT

The present invention relates to a medical Au—Pt—Pd alloy including Au, Pt, Pd, and inevitable impurities. The alloy has an alloy composition inside a polygon (A1-A2-A3-A4-A5-A6) surrounded by straight lines connected at point A1 (Au: 37.9 atom %, Pt: 0.1 atom %, and Pd: 62 atom %), point A2 (Au: 79.9 atom %, Pt: 0.1 atom %, and Pd: 20 atom %), point A3 (Au: 79.9 atom %, Pt: 20 atom %, and Pd: 0.1 atom %), point A4 (Au: 69.9 atom %, Pt: 30 atom %, and Pd: 0.1 atom %), point A5 (Au: 49 atom %, Pt: 30 atom %, and Pd: 21 atom %), and point A6 (Au: 39 atom %, Pt: 40 atom %, and Pd: 21 atom %) in a Au—Pt—Pd ternary state diagram. The metal structure of the alloy is optimized, and the metal (Continued)

structure is close to a single-phase structure, and has little precipitation of a Au-rich phase and a Pt-rich phase different in composition from a mother phase.

16 Claims, 4 Drawing Sheets

(56) References Cited

U.S. PATENT DOCUMENTS

| | | | |
|---|---|---|---|
| 5,472,333 A * | 12/1995 | van der Zel | .............. C22C 5/02 |
| | | | 425/464 |
| 10,220,120 B2 * | 3/2019 | Shima | ..................... A61L 29/02 |
| 10,883,162 B2 * | 1/2021 | Shima | ........................ C22C 5/02 |
| 2005/0121120 A1 * | 6/2005 | Van Dijk | .............. A61L 27/047 |
| | | | 148/678 |
| 2017/0029927 A1 | 2/2017 | Shima et al. | |
| 2021/0047717 A1 | 2/2021 | Shima et al. | |

FOREIGN PATENT DOCUMENTS

| | | |
|---|---|---|
| JP | 5582484 B1 | 9/2014 |
| JP | 2015-120946 A | 7/2015 |
| JP | 2016-094656 A | 5/2016 |
| JP | 2016-130351 A | 7/2016 |
| WO | WO-2008/032370 A1 | 3/2008 |
| WO | WO-2015/093064 A1 | 6/2015 |

OTHER PUBLICATIONS

International Searching Authority, "International Search Report," issued in connection with International Patent Application No. PCT/JP2020/035903, dated Oct. 27, 2020.

International Searching Authority, "Written Opinion," issued in connection with International Patent Application No. PCT/JP2020/035903, dated Oct. 27, 2020.

Japanese Patent Office, "Decision to Grant a Patent," issued in connection with Japanese Patent Application No. 2019-175208, dated Oct. 19, 2020.

Extended European Search Report issued in corresponding European Patent Application No. 20870318.1 dated Jul. 22, 2022.

Guerin, S., et al., "High-Throughput Synthesis and Screening of Ternary Metal Alloys for Electrocatalysis," J. Phys. Chem. B 110(29):14355-14362 (2006).

Zou, S., et al., "Fabricating the AuPdPt Ternary Nanophase Diagram at 800 °C To Guide the Exploration of Optimal Catalyst for n-Hexane Oxidation," J. Phys. Chem. C., 121(7):4074-4082 (2017).

\* cited by examiner

MEDICAL AU-PT-PD ALLOY

CROSS-REFERENCE TO RELATED APPLICATIONS

The present application claims priority under 37 U.S.C. § 371 to International Patent Application No. PCT/JP2020/035903, filed Sep. 24, 2020, which claims priority to and the benefit of Japanese Patent Application No. 2019-175208, filed on Sep. 26, 2019. The contents of these applications are hereby incorporated by reference in their entireties.

TECHNICAL FIELD

The present invention relates to a Au—Pt—Pd alloy suitable as a medical material which forms medical equipment such as an embolization coil or an embolization clip. In particular, the present invention relates to a medical material causing less artifacts in a magnetic field environment and having excellent mechanical properties, and a method for producing the medical material.

BACKGROUND ART

Attention is being paid to usefulness of endovascular treatment as a method for treating a cerebrovascular disorder such as brain aneurysm or subarachnoid hemorrhage. As medical equipment in treatment methods such as the endovascular treatment, various forms of medical equipment such as embolization coils, embolization clips, stents, catheters, and coils are applied. Since the medical equipment is a device which comes into direct contact with a human body and is embedded in the human body, the medical equipment is required to have biocompatibility and chemical stability (corrosion resistance). In addition, embolization coils etc. which are applied to the inside of pulsative and pulsatory blood vessels are required to have mechanical properties such as strength and a spring property. With consideration given to these demand characteristics, various metal materials such as Pt—W alloys (e.g. Pt-8 mass % W alloys), Ti alloys (e.g. Ti-6 mass % Al-4 mass % V alloys), and stainless steel (e.g. SUS 316L) have been applied.

In medical settings in recent years, diagnoses and treatments using magnetic resonance imaging diagnostic processors (MRI) have been extensively carried out, and impacts of the medical material in a magnetic field environment have been a concern. Examples of the characteristics of metal materials which are considered as a concern in the magnetic field environment include magnetic susceptibility. The reason why the magnetic susceptibility of the metal material is a concern is that the metal material causes magnetic susceptibility artifacts (false images) in MRI. The magnetic susceptibility artifact (hereinafter, referred to an "artifact") is a phenomenon in which a difference between the magnetic susceptibility of a metal in a magnetic field and the magnetic susceptibility of a biological tissue in a peripheral region of the metal causes a distortion in a MRI image. Generation of artifacts hampers accurate operations and diagnoses.

Here, many of the above-described proven medical metal materials have large magnetic susceptibility with respect to the magnetic susceptibility of biological tissues. In this connection, adjustment of parameters in an MRI apparatus, or the like has been performed as a conventional method for coping with artifacts from medical equipment in MRI. However, it can be hardly said that adjustment for the MRI apparatus is a fundamental solution against artifacts. In addition, MRI apparatuses have been directed to having a superhigh magnetic field in order to enhance the definition for securing accuracy of diagnosis etc. and enhance the speed. For apparatuses with a superhigh magnetic field, the artifact problem cannot be solved by conventional coping methods.

The present applicant has proposed a Au—Pt alloy containing a predetermined amount of Pt and Au as a balance for coping with the artifact problem with medical metal materials (Patent Document 1). The Au—Pt alloy is a metal material whose magnetic susceptibility is adjusted to fall within a suitable range by controlling a metal structure while alloying Pt with Au which is a diamagnetic metal.

RELATED ART DOCUMENT

Patent Document

Patent Document 1: JP 5582484 B2

SUMMARY OF THE INVENTION

Problems to be Solved by the Invention

A medical metal material including the above-described conventional Au—Pt alloy is a one which can be referred to as "artifactless" as the magnetic susceptibility is extremely close to the magnetic susceptibility (−9 ppm ((−9×10$^{-6}$)) of water which is a main constituent of biological tissues. However, the alloy is inferior in mechanical characteristics to conventional materials, and it is difficult to apply the alloy to medical equipment. For example, for the above-described embolization coil, high strength and a spring property are required, and a Pt-8 mass % W alloy has been heretofore used. The Au—Pt alloy has lower mechanical properties as compared to the Pt-8 mass % W alloy, and is therefore difficult to apply to the embolization coils.

The present invention has been made in view of the above-described situations, and an object of the present invention is to provide a medical metal material which is probably used in a magnetic field environment with MRI etc. The medical metal material is a medical alloy material having preferred magnetic susceptibility to improve the artifact problem and having excellent mechanical properties.

Means for Solving the Problems

The present inventors conducted studies for finding a material capable of solving the above-described problems. In the studies, the above-described Au—Pt alloy was used as a base, and Pd was added to this alloy as an additive for improving mechanical properties.

On the other hand, Pd is a paramagnetic metal element, and therefore shifts the magnetic susceptibility of an alloy in a positive direction. Thus, excessive addition of Pd eliminates the artifactless characteristic of the Au—Pt alloy.

For a Au—Pt—Pd alloy obtained by adding Pd to the Au—Pt alloy, the present inventors adjusted an alloy composition and a metal structure, and examined an effect on magnetic susceptibility and mechanical properties. As a result, they found a range enabling exhibition of preferred characteristics, and in this way, attained the present invention.

Specifically, the present invention provides a medical Au—Pt—Pd alloy including Au, Pt, Pd, and inevitable impurities. The medical Au—Pt—Pd alloy has an alloy composition inside a polygon (A1-A2-A3-A4-A5-A6) surrounded by straight lines connected at point A1 (Au: 37.9 atom %, Pt: 0.1 atom %, and Pd: 62 atom %), point A2 (Au: 79.9 atom %, Pt: 0.1 atom %, and Pd: 20 atom %), point A3 (Au: 79.9 atom %, Pt: 20 atom %, and Pd: 0.1 atom %), point A4 (Au: 69.9 atom %, Pt: 30 atom %, and Pd: 0.1 atom %), point A5 (Au: 49 atom %, Pt: 30 atom %, and Pd: 21 atom %), and point A6 (Au: 39 atom %, Pt: 40 atom %, and Pd: 21 atom %) in a Au—Pt—Pd ternary state diagram. In a metal structure on any cross-section, with respect to a composition of a Au—Pt—Pd alloy as a mother phase, a total of an area ratio of a Au-rich phase which is an alloy phase having a Au content higher by 4 atom % or more than that of the mother phase and an area ratio of a Pt-rich phase which is an alloy phase having a Pt content higher by 4 atom % or more than that of the mother phase is 1.4% or less.

As described above, the present inventive medical alloy material includes a Au—Pt—Pd alloy having an alloy composition within a certain composition range, and having a metal structure in which precipitation and distribution of a Au-rich phase and a Pt-rich phase different in composition from a mother phase are suppressed. Hereinafter, the constitutions of the present invention will be described in detail. In the following description, the Au-rich phase and the Pt-rich phase are sometimes referred to as separate phases.

(A) Alloy Composition (A-1) Composition Range of Essential Elements

Figure 1:
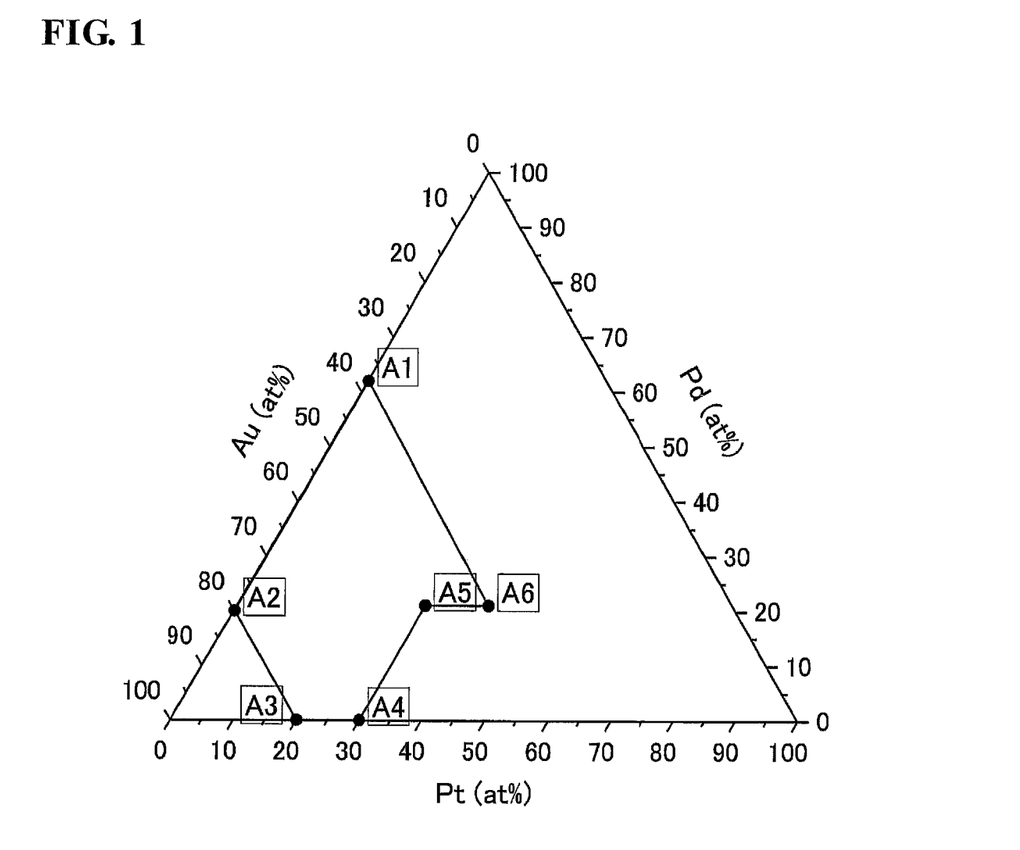
FIG. 1 is a ternary state diagram of a Au—Pt—Pd alloy, which also shows a composition range (A1-A2-A3-A4-A5-A6: good region) of the present inventive alloy.

As described above, the present inventive medical Au—Pt—Pd alloy has a composition inside a polygon surrounded by point A1 (Au: 37.9 atom %, Pt: 0.1 atom %, and Pd: 62 atom %), point A2 (Au: 79.9 atom %, Pt: 0.1 atom %, and Pd: 20 atom %), point A3 (Au: 79.9 atom %, Pt: 20 atom %, and Pd: 0.1 atom %), and point A4 (Au: 69.9 atom %, Pt: 30 atom %, and Pd: 0.1 atom %), point A5 (Au: 49 atom %, Pt: 30 atom %, and Pd: 21 atom %), and point A6 (Au: 39 atom %, Pt: 40 atom %, and Pd: 21 atom %) (FIG. 1). This composition range and a metal structure (suppression of separate phases) as described later enable the alloy to have a good balance in terms of magnetic susceptibility and mechanical properties. There remains a possibility that alloys having a composition outside the above-mentioned range is inferior in magnetic susceptibility and strength to conventional arts. Specifically, for magnetic susceptibility, alloys having a composition outside the above-mentioned range cause artifacts as easily as or more easily than the Pt—W alloy which is a conventional art. For strength, alloys having a composition outside the above-mentioned range have strength lower than that of the Au—Pt alloy which is a basic alloy of the present invention. The alloy outside this composition range may undergo precipitation of separate phases (Au-rich phase and Pt-rich phase) in a state after solution treatment in a production process as described later. In the following description, the composition range surrounded by point A1-point A2-point A3-point A4-point A5-point A6 is sometimes referred to as a "good region".

Figure 2:
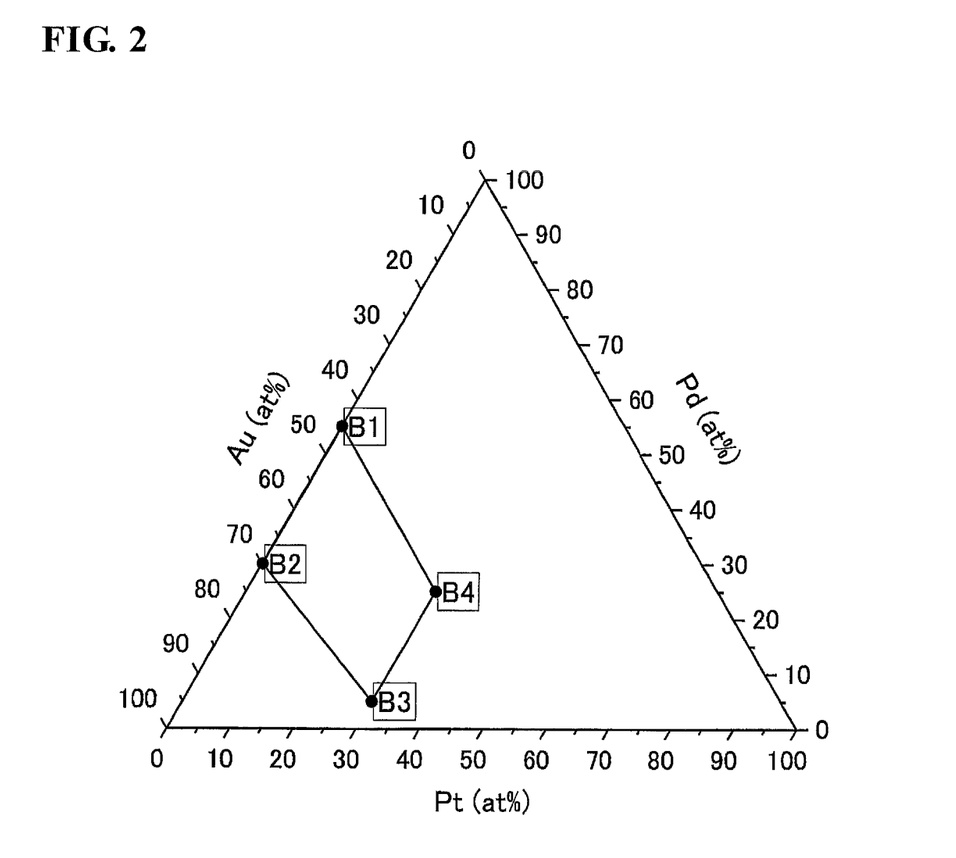
FIG. 2 is a ternary state diagram of a Au—Pt—Pd alloy, which also shows the composition range (B1-B2-B3-B4: better region) of the present inventive alloy.

Preferably, the Au—Pt—Pd alloy having an alloy composition within the above-mentioned range has an alloy composition inside a polygon surrounded by point B1 (Au: 44.9 atom %, Pt: 0.1 atom %, and Pd: 55 atom %), point B2 (Au: 69.9 atom %, Pt: 0.1 atom %, and Pd: 30 atom %), point B3 (Au: 65 atom %, Pt: 30 atom %, and Pd: 5 atom %), and point B4 (Au: 45 atom %, Pt: 30 atom %, and Pd: 25 atom %). The alloy composition allows the alloy to have a composition within a range narrower than the above-mentioned range and exhibit more preferred magnetic susceptibility and mechanical strength. In the following description, the composition range surrounded by point B1-point B2-point B3-point B4 is sometimes referred to as a "better region".

Figure 3:
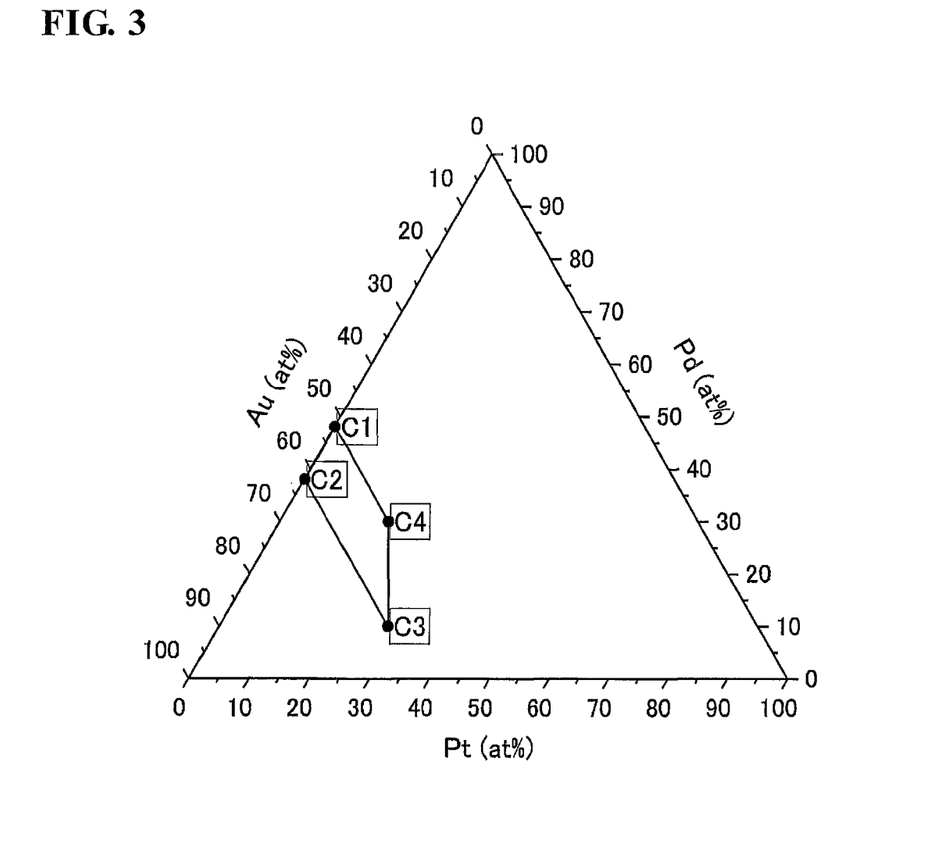
FIG. 3 is a ternary state diagram of a Au—Pt—Pd alloy, which also shows the composition range (C1-C2-C3-C4: best region) of the present inventive alloy.

The Au—Pt—Pd alloy is particularly preferably an alloy having an alloy composition within the above-mentioned range inside a polygon surrounded by point C1 (Au: 51.9 atom %, Pt: 0.1 atom %, and Pd: 48 atom %), point C2 (Au: 61.9 atom %, Pt: 0.1 atom %, and Pd: 38 atom %), point C3 (Au: 62 atom %, Pt: 28 atom %, and Pd: 10 atom %), and point C4 (Au: 52 atom %, Pt: 18 atom %, and Pd: 30 atom %). The alloy having a composition within a narrower range likely has particularly preferred magnetic susceptibility and mechanical strength, and can be expected to have an artifact suppressing effect on a magnetic diagnosis apparatus such as a MRI whose magnetic field will increase in the future. In addition, the alloy is particularly suitable as a constituent material of medical equipment required to have high strength and high elasticity, such as embolization coils. In the following description, the composition range surrounded by point C1-point C2-point C3-point C4 is sometimes referred to as a "best region".

(A-2) Range of Arbitrary Elements and Impurity Elements

The present inventive alloy includes a tertiary alloy of Au, Pt, and Pd, and may contain a very small amount of additive elements. Specifically, the alloy may contain Ca and Zr. These additive elements have an effect of increasing the strength of the alloy, etc., and are contained in a total amount of 0 mass % or more and 0.5 mass % or less. The present inventive alloy may contain inevitable impurities. As the inevitable impurities, Ag, Co, Cr, Fe, Ir, Mg, Ni, Rh, Ru, Si, Sn, and Ti may be contained, and the total amount of the inevitable impurities contained may be 0 ppm or more and 200 ppm or less. These additive elements and/or inevitable impurity elements replace a part of Au in the Au—Pt—Pd alloy.

(B) Metal Structure

The present inventive medical Au—Pt—Pd alloy is made to exhibit magnetic properties suitable for medical alloys by setting the composition within the above-mentioned range, and optimizing a metal structure. The optimized metal structure is a metal structure close to a single-phase structure formed of an alloy having the above-mentioned composition, and the structure has little distributions of separate phases different in composition from the mother phase.

The mother phase refers to a phase of a Au—Pt—Pd alloy constituting a matrix of the metal structure, and is an alloy layer having a composition identical or substantially identical to the alloy composition of the Au—Pt—Pd alloy. Specifically, the mother phase is an alloy phase in which the content of each of Au and Pt is within the range of ±3 atom % with respect to the overall composition of the Au—Pt—Pd alloy. The mother phase is an alloy of a supersaturated solid solution obtained by subjecting a melted and cast alloy to homogenization treatment and solution treatment in a method for producing an alloy as described later.

The Au-rich phase is an alloy phase having a Au content higher by 4 atom % or more than the Au content of the mother phase. The Au-rich phase is basically a Au—Pt—Pd alloy. While having a Au content higher than that of the mother phase, the Au-rich phase has a Pt content lower than that of the mother phase and a Pd content close to that of the mother phase. The Pt content of the Au-rich phase is lower by 4 atom % or more than the Pt content of the mother phase. The Pd content of the Au-rich phase is within the range of ±2 atom % with respect to the Pd content of the mother phase.

The Pt-rich phase is an alloy phase having a Pt content higher by 4 atom % or more than the Pt content of the mother phase. The Pt-rich phase is basically a Au—Pt—Pd alloy.

While having a Pt content higher than that of the mother phase, the Pt-rich phase has a Au content lower than that of the mother phase and a Pd content close to that of the mother phase. The Au content of the Pt-rich phase is lower by 4 atom % or more than the Au content of the mother phase. The Pd content of the Au-rich phase is within the range of ±2 atom % with respect to the Pd content of the mother phase.

In the present invention, the amount of separate phases including the Au-rich phase and the Pt-rich phase is limited. Specifically, the total area ratio of the Au-rich phase and the Pt-rich phase is 1.4% or less. By setting the ratio of separate phases to 1.4% or less in the Au—Pt—Pd alloy having the above-mentioned composition, the volume magnetic susceptibility of the alloy can be stabilized. The reason why magnetic characteristics are stabilized by making the metal structure close to a single-phase state is considered that thanks to the small amount of separate phases, the crystal grain boundary energy is low, thereby crystal grains are stable. In the present invention, it is not necessary to separately define the area ratio of the Au-rich phase and the area ratio of the Pt-rich phase.

In the present invention, the area ratio refers to one based on the observation visual field in observation of a material structure on any cross-section. As indicated by "any cross-section", the cut section or the cutting direction during observation is not specified. In addition, in the present inventive Au—Pt—Pd alloy, the area ratio of a predetermined separate phase is determined, but an observation visual field is not selected in such a manner as to intentionally exclude the separate phase. The size of the observation visual field is preferably in a range of 10,000 to 50,000 $\mu m^2$. For calculation of the area ratio of separate phases in the alloy, area ratios for cross-sections at a plurality of arbitrary positions may be measured, followed by calculating an average of the area ratios. For measurement of the area ratio of the separate phases, image processing software or the like may be used.

(C) Magnetic and Mechanical Properties of Alloy

The present inventive Au—Pt—Pd alloy has magnetic susceptibility enabling suppression of artifacts, and mechanical properties required as medical equipment. As specific magnetic and mechanical properties of the present inventive Au—Pt—Pd alloy, the volume magnetic susceptibility is −32 ppm or more and 60 ppm or less, and the Young's modulus is 100 GPa or more. As preferred values of the magnetic and mechanical properties, the magnetic susceptibility is −32 ppm or more and 30 ppm or less, and the Young's modulus is 110 GPa or more. Particularly preferably, the magnetic susceptibility is −20 ppm or more and 0 ppm or less, and the Young's modulus is 130 GPa or more. In addition, the magnetic properties and the mechanical properties of the present inventive Au—Pt—Pd alloy can vary basically depending on both the alloy composition and the material structure (e.g. total area ratio of separate phases).

(D) Method for Producing Present Inventive Au—Pt—Pd Alloy

A method for producing the present inventive Au—Pt—Pd alloy will now be described. The method for producing the present inventive alloy includes the steps of: melting and casting a mother alloy having a composition within the above-mentioned range; subjecting the mother alloy to homogenization treatment; subjecting to plastic working the mother alloy subjected to the homogenization treatment; and subjecting to solution treatment the alloy subjected to plastic working. These steps will be described.

Methods and conditions in melting and casting methods can be applied to the melting and casting step for producing the mother alloy. For adjustment of the alloy composition, raw metals of Au, Pt, and Pd can be mixed at the above-mentioned composition, and melted and cast by arc melting, high-frequency melting or the like to produce an ingot of the mother alloy.

The homogenization treatment refers to a treatment step for homogenizing the metal structure by heating the mother alloy produced in the melting and casting step. The homogenization treatment is important in adequate formation of a solid solution by subsequent solution treatment. In the present invention, Pd is added to a conventional Au—Pt alloy, and as the number of constituent elements increases, atom transfer of the constituent elements by the homogenization treatment becomes more important. In addition, by performing the homogenization treatment, processability in plastic working in the step can be improved. As a condition for the homogenization treatment, the treatment temperature is preferably 1,000° C. or higher and 1,200° C. or lower. In the homogenization heat treatment, the higher the temperature, the more efficient. This is because in a Au—Pt—Pd ternary system, there is a composition range where the alloy melts at 1,200° C. The treatment time is preferably 1 hour or more and 48 hours or less.

A plastic working step and a solution treatment step are carried out on the homogenization-treated mother alloy, and the alloy is formed into a supersaturated solid solution. The present inventive alloy is an alloy having a metal structure close to a single-phase state, and production of the alloy requires homogenization treatment and treatment with a plastic working step added to a solution treatment step.

The plastic working step refers to a step for introducing a drive force for generation of a solid solution by solution treatment. In addition, the plastic working step serves as a step of preliminarily adjusting a size and a shape before forming the alloy into a final shape. The plastic working is preferably cold working in which the working temperature is ordinary temperature or hot working in which the working temperature is 400° C. or lower. The working rate is preferably 30% or more and 90% or less. However, the form of the working is not limited, but various forms of working methods such as swaging, rolling, casting, wire drawing, and extrusion are applied.

For the heat treatment in the solution treatment step, the plastically-worked mother alloy is heated to 1,000° C. or higher and 1,200° C. or lower. The heating time during heating is preferably 1 to 24 hours. In addition, it is preferable to adopt rapid as cooling after heating and to put the alloy in a cooling medium such as water within 3 seconds or less after the heating. The number of treatments for single-phasing by combining the above plastic working and solution treatment may be one, or two or more.

In the supersaturated solid solution alloy obtained in the manner described above, generation/distribution of separate phases such as a Au-rich phase and a Pt-rich phase is suppressed. The supersaturated solid solution alloy has preferred volume magnetic susceptibility and mechanical properties. The alloy also has good processability, and can be processed into any shape such as a wire material, and used for various purposes.

Further, additional heat treatment may be performed on the present inventive alloy obtained by a combination of the plastic working step and the solution treatment step. The additional heat treatment may cause movement of atoms in the alloy, resulting in exhibition of such effects as adjustment of magnetic susceptibility and improvement in strength. The temperature in the additional heat treatment is preferably in a range of 400 to 800° C. The heat treatment time is preferably 0.5 to 48 hours.

When the additional heat treatment is performed, plastic working may be performed before the heat treatment. In this case, cold working at one time (one pass) or more is preferable, and the working form may be any of swaging, rolling, casting, wire drawing, extrusion, and the like. In addition, the working rate per pass is preferably 12 to 18%. When working at a plurality of passes is performed, the total working rate is preferably 50% or more. However, the additional heat treatment and the plastic working before the heat treatment do not always exhibit an effect, and are therefore optional steps.

Examples of the medical equipment to which the above-described present inventive medical Au—Pt—Pd alloy is suitably applied include various forms of medical equipment such as coils such as embolization coils, embolization clips, stents such as flow diverter stents and stent retrievers, and catheters such as balloon catheters.

For application to such medical equipment, the shape of the alloy of the present invention is not limited, and the alloy is processed into various forms such as those of wire materials, bar materials, square materials, hollow materials, and plate materials. For example, for the embolization coil, the alloy is processed into a wire material, and then molded by a winding machine to prepare a coil. The stent is prepared by using a knitting machine to knit the alloy processed into a wire material. The stent retriever is prepared by molding the alloy processed into a pipe material or a tube material. The present inventive Au—Pt—Pd alloy has good processability, and can be processed into various shapes as described above.

Advantageous Effects of the Invention

As described above, the present inventive Au—Pt—Pd alloy has magnetic susceptibility suitable as a medical metal material, and is improved in terms of the artifact problem in magnetic diagnosis equipment such as a MRI. The alloy is excellent in mechanical properties, and has good strength, operability, and durability when used in various kinds of medical equipment.

DESCRIPTION OF EMBODIMENTS

Hereinafter, an embodiment of the present invention will be described. In this embodiment, Au—Pt—Pd alloys of various compositions were produced, and evaluated for magnetic characteristics and mechanical characteristics.

For the Au—Pt—Pd alloys, raw metals of pure Au, pure Pt, and pure Pd with a purity of 99.99% were weighed to various compositions, and melted at a high frequency and cast into an alloy ingot (crucible: zirconia crucible, mold: water-cooled Cu mold, maximum power during melting: 2.5 kW). A mother alloy ingot of 7 mm (diameter)×65 mm was produced by the melting and casting step.

Next, the mother alloy was subjected to homogenization treatment in which the alloy was heated in an Ar atmosphere at 1,100° C. for 1 hour. After the heating, the mother alloy was cooled with water.

The mother alloy after the homogenization treatment was subjected to plastic working and solution treatment. In the plastic working step, swaging was performed at ordinary temperature, and the ingot with a diameter of 7 mm was reduced in diameter to a diameter of 4 mm in increments of 0.5 mm to 1 mm. The processed mother alloy was heated in an Ar atmosphere at a temperature of 1,100° C. for 12 hours, and then rapidly cooled to perform solution treatment.

The mother alloy (diameter: 4 mm) obtained after the solution treatment was subjected to wire drawing at a working rate of 10% per pass until the diameter was 3 mm. In this way, a sample was obtained.

For the Au—Pt—Pd alloys produced in this embodiment, cross-sections were observed by SEM to examine metal structures. In the structure observation, a sample obtained by cutting the wire material at any position was polished into a mirror surface state, and subjected to ion milling to make the surface state easily observable. The sample was then observed by SEM.

In observation of separate phases which are an Au-rich phase and a Pt-rich phase, the Au-rich phase and the Pt-rich phase were identified with respect to a matrix phase by SEM-EDX composition analysis (accelerating voltage: 15 kV). In addition, when there was a sample in which it was difficult to identify the Au-rich phase and the Pt-rich phase, a surface of the sample was observed by EPMA (accelerating voltage: 15 kV), and mapping was performed to identify the phases. The area ratios of the Au-rich phase and the Pt-rich phase were determined by image evaluation. For the image evaluation, the area ratios of the separate phases were calculated by use of the crystal grain evaluation tool: Grain Expert which is commercially available image analysis software (Leica Application Suite manufactured by Leica).

Further, the Au—Pt—Pd alloys produced in this embodiment were subjected to volume magnetic susceptibility measurement, processability evaluation, and mechanical property evaluation. For the volume magnetic susceptibility measurement, a sample of 3 mm (diameter)×8 mm was prepared, and volume magnetic susceptibility (Xv) was measured at room temperature (25° C.) by use of a high-sensitivity small magnetic balance (MSB-AUTO).

For the processability, whether or not breakage occurred was evaluated in formation of a wire material with a diameter of 1 mm by subjecting a wire material (diameter: 3 mm) to wire drawing at a working rate of 10% per pass. For the mechanical properties, a sample with a diameter of 1 mm was set with a chuck-to-chuck distance of 100 mm in a tensile tester, and a tension test was conducted at a cross head speed of 1 mm/min to measure a Young's modulus.

Figure 4:
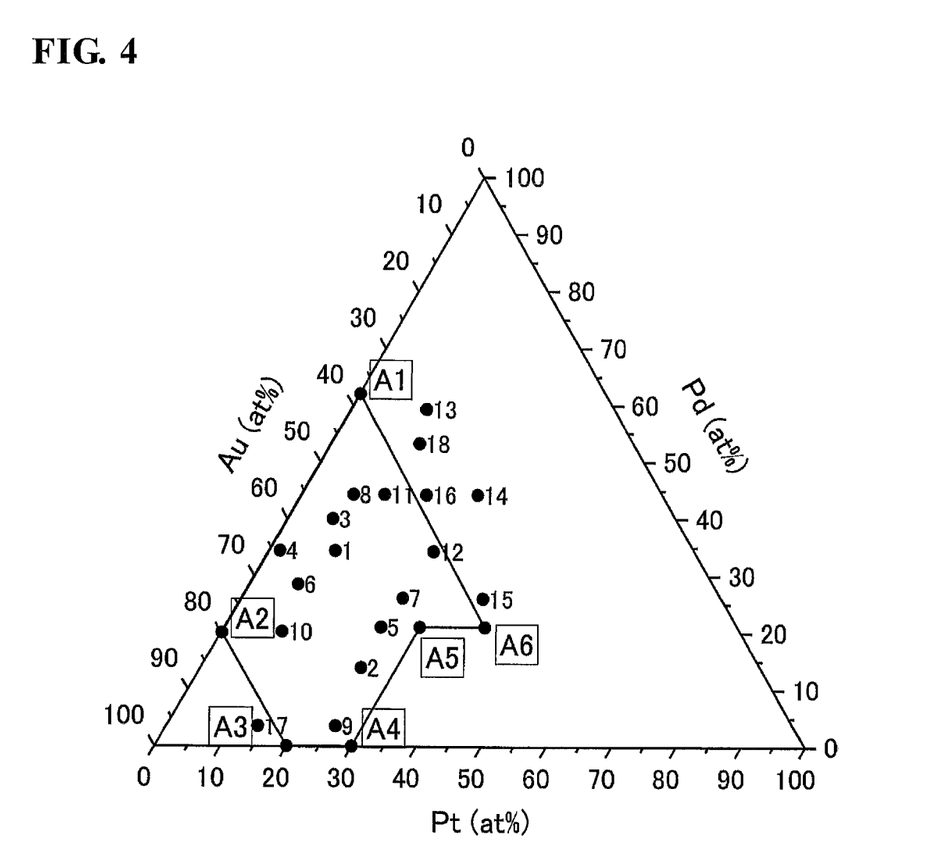
FIG. 4 is a ternary state diagram showing a composition of a Au—Pt—Pd alloy produced in an embodiment.

Table 1 shows the evaluation results of various Au—Pt—Pd alloys produced in this embodiment. In addition The compositions of the Au—Pt—Pd alloys produced in this embodiment are shown in a ternary state diagram of FIG. 4.

TABLE 1

| No. | Composition (at %) Au | Pt | Pd | Total area ratio of separate phases (%) | Xv (ppm) | Young's modulus (GPa) | Processability |
|---|---|---|---|---|---|---|---|
| 1 | Balance | 10.2 | 34.4 | 1.0 | −8 | 131 | ○ |
| 2 | | 24.5 | 13.9 | 0.2 | −10 | 130 | ○ |
| 3 | | 7 | 40 | 1.3 | −2 | 152 | ○ |
| 4 | | 1.7 | 34.4 | 0.4 | −31 | 131 | ○ |
| 5 | | 24 | 21 | 1.4 | 7 | 150 | ○ |
| 6 | | 7.5 | 28.5 | 1.4 | −28 | 129 | ○ |
| 7 | | 24.8 | 26.1 | 1.1 | 24 | 138 | ○ |
| 8 | | 8 | 44.3 | 0.1 | 25 | 121 | ○ |
| 9 | | 25.8 | 3.6 | 0.2 | −23 | 101 | ○ |
| 10 | | 9.2 | 20.2 | 0.4 | −29 | 104 | ○ |
| 11 | | 12.8 | 44.3 | 0.1 | 50 | 130 | ○ |
| 12 | | 25.4 | 34.3 | 0.0 | 58 | 128 | ○ |
| 13 | Balance | 11.7 | 59.3 | 0.6 | 138 | 136 | ○ |
| 14 | | 27.2 | 44.2 | 0.1 | 117 | 133 | ○ |
| 15 | | 37.2 | 26.0 | 0.2 | 69 | 148 | ○ |
| 16 | | 19.3 | 44.2 | 0.4 | 79 | 163 | ○ |
| 17 | | 13.9 | 3.6 | 2.6 | −29 | 85 | ○ |
| 18 | | 13.7 | 53.2 | 2.0 | 104 | 142 | ○ |

TABLE 2

| | Composition (at %) | | | Xv (ppm) | | | Youngs modulus (GPa) | | | Area ratio of seperate phases | |
|---|---|---|---|---|---|---|---|---|---|---|---|
| No. | Au | Pt | Pd | Before heat treatment | After heat treatment | Width of change | Before heat treatment | After heat treatment | Width of change | Before heat treatment | After heat treatment |
| 4 | Balance | 1.7 | 34.4 | −31 | −27 | +4 | 131 | 144 | +13 | 0.44 | 0.26 |
| 7 | | 24.8 | 26.1 | 24 | 31 | +7 | 138 | 137 | −1 | 1.07 | 0.90 |
| 8 | | 8 | 44.3 | 25 | 26 | +1 | 121 | 153 | +32 | 0.09 | 0.17 |
| 9 | | 25.8 | 3.6 | −23 | −10 | +13 | 101 | 105 | +4 | 0.15 | 1.28 |
| 10 | | 9.2 | 20.2 | −29 | −25 | +4 | 104 | 117 | +13 | 0.41 | 0.37 |
| 11 | | 12.8 | 44.3 | 50 | 51 | +1 | 130 | 148 | +18 | 0.08 | 0.43 |

It will be apparent from Table 1 that in a region surrounded by point A1-point-A2-point-A3-point-A4-point A5-point A6 (good region) in the ternary state diagram specified in the present application, the volume magnetic susceptibility of the Au—Pt—Pd alloy is within a range of −32 ppm or more and 60 ppm or less, and the Young's modulus is 100 GPa or more (Nos. 1 to 12).

Au—Pt—Pd alloys with an alloy composition range in a better region or a best region narrower than the good region tend to exhibit a more preferred volume magnetic susceptibility and Young's modulus (Nos. 1 to 8). The alloys of Nos. 1 to 3 are alloys which have a particularly good volume magnetic susceptibility and Young's modulus, and have a volume magnetic susceptibility of −10 ppm or less, so as to be artifactless.

On the other hand, alloys with a composition outside the composition range specified in the present invention tend to have a volume magnetic susceptibility of more than 60 ppm (Nos. 13 to 16). These alloys have a low area ratio of separate phases, and have high magnetic susceptibility depending on compositions. Even when the amount of Pd is reduced as compared to the alloys of Nos. 13 to 16, the Young's modulus decreases although the magnetic susceptibility shifts to a negative side if the composition is outside the range specified in the present invention (No. 17). Further, alloys whose composition and area ratio of separation phases are outside the specified ranges and whose magnetic susceptibility is excessively high, like the alloy of No. 18, were observed.

Second Embodiment

In this embodiment, the Au—Pt—Pd alloys of Nos. 4, 7, 8, 9, 10, and 11 produced in the first embodiment were subjected to heat treatment, and various characteristics were evaluated. In the heat treatment, the alloy was heated in an Ar atmosphere at a temperature of 600° C. for 1 hour, and then rapidly cooled to obtain a Au—Pt—Pd alloy wire material sample. The evaluation results are shown in Table 2.

From Table 2, it is thought that heat treatment of an alloy subjected to solution treatment tends to shift the volume magnetic susceptibility to a positive side. Hence, the volume magnetic susceptibility of the alloy of No. 9 is made to fall within the best range of −20 ppm to 0 ppm. Accordingly, the heat treatment after the solution treatment has a certain technical significance. Even this heat treatment does not cause a dramatic change in metal structure of the alloy, and a pseudo single-phase state is maintained.

In addition, the width of change in magnetic susceptibility after heat treatment differs depending on the alloy composition. As a tendency thereof, alloys having a low Pd content have a large width of change, and alloys having a high Pd content do not have a so large width of change. The action of the heat treatment is as described above, and alloys having a small change in magnetic susceptibility after heat treatment are thermally stable, and therefore suitable for applications in which heat may be further applied after product processing. For example, for an embolization coil, a wire material is formed into a primary coil, and further processed into a secondary coil to be used. Processing of the secondary coil involves heating, and therefore alloys having a small change in magnetic susceptibility are effective in the above-mentioned applications. On the other hand, alloys whose magnetic susceptibility is suitably changed by heat treatment can be formed into artifactless products.

INDUSTRIAL APPLICABILITY

The present inventive medical Au—Pt—Pd alloy is suitable as a constituent material for medical equipment which is used in a magnetic field environment. The alloy of the present invention is capable of coping with the artifact problem, and has mechanical properties required for various kinds of medical equipment. The present invention can be expected to be applied to various kinds of medical equipment such as coils such as embolization coils, stents, catheters, and guide wires.

The invention claimed is:

1. A medical Au—Pt—Pd alloy comprising Au, Pt, Pd, and inevitable impurities, wherein the medical Au—Pt—Pd alloy has an alloy composition inside a polygon (A1-A2-A3-A4-A5-A6) surrounded by straight lines connected at point A1 (Au: 37.9 atom %, Pt: 0.1 atom %, and Pd: 62 atom %), point A2 (Au: 79.9 atom %, Pt: 0.1 atom %, and Pd: 20 atom %), point A3 (Au: 79.9 atom %, Pt: 20 atom %, and Pd: 0.1 atom %), point A4 (Au: 69.9 atom %, Pt: 30 atom %, and Pd: 0.1 atom %), point A5 (Au: 49 atom %, Pt: 30 atom %, and Pd: 21 atom %), and point A6 (Au: 39 atom %, Pt: 40 atom %, and Pt: 21 atom %) in a Au—Pt—Pd ternary state diagram, and in a metal structure on any cross-section, with a composition of a mother phase Au—Pt—Pd alloy as a criterion, a total of an area ratio of a Au-rich phase which is an alloy phase having a Au content higher by 4 atom % or more than that of the mother phase and an area ratio of a Pt-rich phase which is an alloy phase having a Pt content higher by 4 atom % or more than that of the mother phase is 1.4% or less.

2. The medical Au—Pt—Pd alloy according to claim 1, which has an alloy composition within the range inside a polygon (B1-B2-B3-B4) surrounded by straight lines connected at point B1 (Au: 44.9 atom %, Pt: 0.1 atom %, and Pd: 55 atom %), point B2 (Au: 69.9 atom %, Pt: 0.1 atom %, and Pd: 30 atom %), point B3 (Au: 65 atom %, Pt: 30 atom %, and Pd: 5 atom %), and point B4 (Au: 45 atom %, Pt: 30 atom %, and Pd: 25 atom %) in the Au—Pt—Pd ternary state diagram.

3. The medical Au—Pt—Pd alloy according to claim 1, which has an alloy composition within the range inside a polygon (C1-C2-C3-C4) surrounded by straight lines connected at point C1 (Au: 51.9 atom %, Pt: 0.1 atom %, and Pd: 48 atom %), point C2 (Au: 61.9 atom %, Pt: 0.1 atom %, and Pd: 38 atom %), point C3 (Au: 62 atom %, Pt: 28 atom %, and Pd: 10 atom %), and point C4 (Au: 52 atom %, Pt: 18 atom %, and Pd: 30 atom %) in the Au—Pt—Pd ternary state diagram.

4. The medical Au—Pt—Pd alloy according to claim 1, wherein a volume magnetic susceptibility of −32 ppm or more and 60 ppm or less and a Young's modulus of 100 GPa or more.

5. The medical Au—Pt—Pd alloy according to claim 2, wherein a volume magnetic susceptibility of −32 ppm or more and 60 ppm or less and a Young's modulus of 100 GPa or more.

6. The medical Au—Pt—Pd alloy according to claim 3, wherein a volume magnetic susceptibility of −32 ppm or more and 60 ppm or less and a Young's modulus of 100 GPa or more.

7. A medical device comprising the medical Au—Pt—Pd alloy defined in claim 1.

8. The medical device according to claim 7, wherein the medical device is one of a stent, a catheter, an embolization coil, an embolization clip, and a guide wire.

9. A medical device comprising the medical Au—Pt—Pd alloy defined in claim 2.

10. A medical device comprising the medical Au—Pt—Pd alloy defined in claim 3.

11. A medical device comprising the medical Au—Pt—Pd alloy defined in claim 4.

12. A method for producing the medical Au—Pt—Pd alloy defined in claim 1, comprising the steps of:

melting and casting a mother alloy of the Au—Pt—Pd alloy;

heating the mother alloy at a temperature of 1,000° C. or higher and 1,200° C. or lower to perform homogenization treatment; and subjecting the homogenization-treated mother alloy to plastic working; and subjecting the plastically-worked alloy to solution treatment.

13. The method for producing the medical Au—Pt—Pd alloy according to claim 12, further comprising a heat treatment step of heating the alloy at 400 to 800° C.

14. A method for producing the medical Au—Pt—Pd alloy defined in claim 2, comprising the steps of:

melting and casting a mother alloy of the Au—Pt—Pd alloy;

heating the mother alloy at a temperature of 1,000° C. or higher and 1,200° C. or lower to perform homogenization treatment; and subjecting the homogenization-treated mother alloy to plastic working; and subjecting the plastically-worked alloy to solution treatment.

15. A method for producing the medical Au—Pt—Pd alloy defined in claim 3, comprising the steps of:

melting and casting a mother alloy of the Au—Pt—Pd alloy;

heating the mother alloy at a temperature of 1,000° C. or higher and 1,200° C. or lower to perform homogenization treatment; and subjecting the homogenization-treated mother alloy to plastic working; and subjecting the plastically-worked alloy to solution treatment.

16. A method for producing the medical Au—Pt—Pd alloy defined in claim 4, comprising the steps of:

melting and casting a mother alloy of the Au—Pt—Pd alloy;

heating the mother alloy at a temperature of 1,000° C. or higher and 1,200° C. or lower to perform homogenization treatment; and subjecting the homogenization-treated mother alloy to plastic working; and subjecting the plastically-worked alloy to solution treatment.

* * * * *